(12) United States Patent
Wright

(10) Patent No.: US 9,752,000 B2
(45) Date of Patent: Sep. 5, 2017

(54) IONOMERIC CROSS-LINKERS AND MEMBRANES FORMED THEREFROM

(71) Applicant: ITM POWER (RESEARCH) LIMITED, South Yorkshire (GB)

(72) Inventor: Shaun Wright, Sosuth Yorkshire (GB)

(73) Assignee: ITM Power (Research) Limited, Sheffield, South Yorkshire (GB)

( * ) Notice: Subject to any disclaimer, the term of this patent is extended or adjusted under 35 U.S.C. 154(b) by 0 days.

(21) Appl. No.: 14/784,692

(22) PCT Filed: Apr. 11, 2014

(86) PCT No.: PCT/GB2014/051151
§ 371 (c)(1),
(2) Date: Feb. 2, 2016

(87) PCT Pub. No.: WO2014/170645
PCT Pub. Date: Oct. 23, 2014

(65) Prior Publication Data
US 2016/0137796 A1 May 19, 2016

(30) Foreign Application Priority Data
Apr. 15, 2013 (GB) .................................. 1306794.7

(51) Int. Cl.
| | |
|---|---|
| *C08J 5/22* | (2006.01) |
| *C07C 209/12* | (2006.01) |
| *C07C 211/63* | (2006.01) |
| *B01D 67/00* | (2006.01) |
| *B01D 71/28* | (2006.01) |
| *B01D 71/82* | (2006.01) |
| *C08F 12/24* | (2006.01) |
| *C08F 12/26* | (2006.01) |
| *C08F 12/34* | (2006.01) |
| *C07C 213/08* | (2006.01) |
| *C07C 215/66* | (2006.01) |
| *C25B 13/08* | (2006.01) |

(52) U.S. Cl.
CPC ........ *C08J 5/2231* (2013.01); *B01D 67/0006* (2013.01); *B01D 71/28* (2013.01); *B01D 71/82* (2013.01); *C07C 209/12* (2013.01); *C07C 211/63* (2013.01); *C07C 213/08* (2013.01); *C07C 215/66* (2013.01); *C08F 12/24* (2013.01); *C08F 12/26* (2013.01); *C08F 12/34* (2013.01); *C25B 13/08* (2013.01); *B01D 2323/30* (2013.01); *B01D 2325/16* (2013.01); *C08J 2325/18* (2013.01)

(58) Field of Classification Search
CPC ... C08J 5/2231; C08J 2325/18; C07C 209/12; C07C 211/63; C07C 213/08; C07C 215/66; B01D 67/0006; B01D 71/28; B01D 71/82; B01D 2323/30; B01D 2325/16; C08F 12/24; C08F 12/26; C08F 12/34; C25B 13/08
USPC .......................................................... 521/27
See application file for complete search history.

(56) References Cited

U.S. PATENT DOCUMENTS

| | | | |
|---|---|---|---|
| 9,073,050 B2 * | 7/2015 | MacDonald | C08J 5/2231 |
| 9,266,069 B2 * | 2/2016 | Higa | |
| 2012/0031834 A1 * | 2/2012 | Higa | B01D 61/44 210/500.42 |
| 2013/0090396 A1 * | 4/2013 | MacDonald | C08J 5/2231 521/27 |

FOREIGN PATENT DOCUMENTS

| | | |
|---|---|---|
| EP | 0919868 A1 | 6/1999 |
| EP | 2420310 A1 | 2/2012 |
| WO | 2013/052227 A1 | 4/2013 |

OTHER PUBLICATIONS

Sinan Korpe et al. "Crosslinked DADMAC polymers as cationic super absorbents". Reactive & Functional Polymers, 69 (2009), pp. 660-665 (www.elsevier.com/locate/react).*
International Search Report dated Aug. 5, 2014 for International Application No. PCT/GB2014/051151.
Sinan Korpe et. al: "Crosslinked DADMAC polymers as cationic super absorbents," Reactive & Functional Polymers, vol. 69, 2009, pp. 660-665, XP002728185.

* cited by examiner

*Primary Examiner* — Michael M Bernshteyn
(74) *Attorney, Agent, or Firm* — Eversheds Sutherland (US) LLP

(57) ABSTRACT

The present invention is the use of a compound comprising two or more covalently bonded polymerisable vinyl groups and one or more covalently bonded ionic groups selected from a quaternary ammonium group; a quaternary phosphonium group; or a tertiary sulphonium group, as an ionic cross-linker. The cross-linkers of the invention may be used to form an ionomer membrane. Methods for forming the cross-linkers of the invention are also disclosed.

17 Claims, 2 Drawing Sheets

IONOMERIC CROSS-LINKERS AND MEMBRANES FORMED THEREFROM

FIELD OF THE INVENTION

Figure 1:
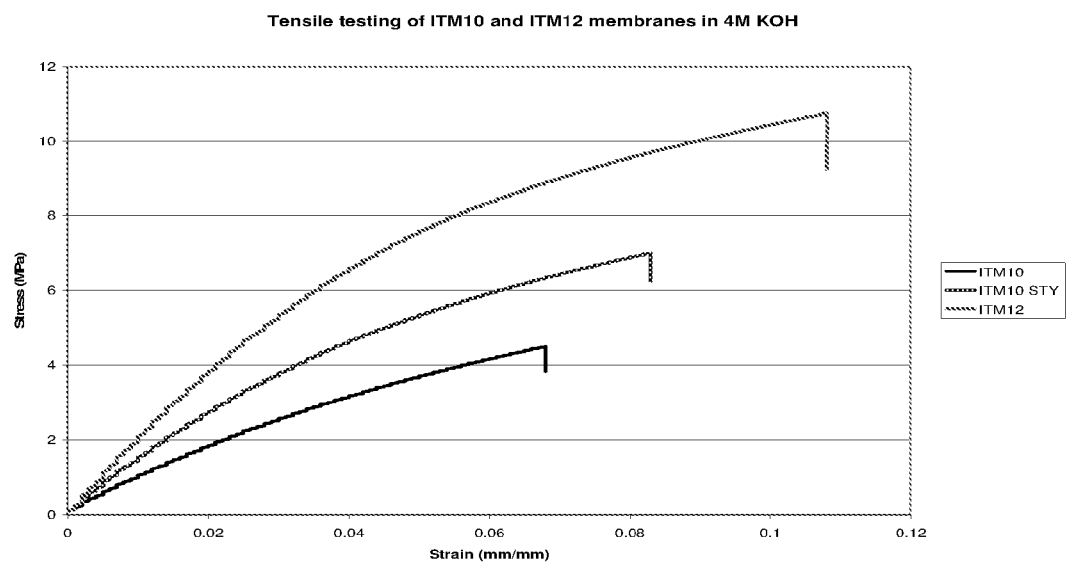

The present invention relates to cross-linkers, suitable for linking polymer chains, and suitable for use in polymer membranes.

BACKGROUND OF THE INVENTION

It is desirable to cross link polymer membranes, in particular hydrophilic polymer membranes, in order to make them stable in electrochemical cells. One cross-linker that is commonly used in anionic membranes is divinylbenzene (DVB). There is a need for an improved cross-linker, for use in polymer membranes.

SUMMARY OF THE INVENTION

It has been surprisingly found that polymer membranes having certain covalently bonded ionic groups are excellent cross-linkers. They produce membranes with superior mechanical properties, greater ionic capacity and greater control of hydration properties.

The principle application for the invention is to enable the development of a solid polymer alkaline electrolyser, which can utilise much lower cost catalyst compare to conventional solid acidic electrochemistry.

According to a first aspect, a compound comprising two or more covalently bonded polymerisable vinyl groups and one or more covalently bonded ionic groups selected from a quaternary ammonium group; a quaternary phosphonium group; or a tertiary sulphonium group, is used as an ionic cross-linker.

According to a second aspect, a compound has the formula I or II:

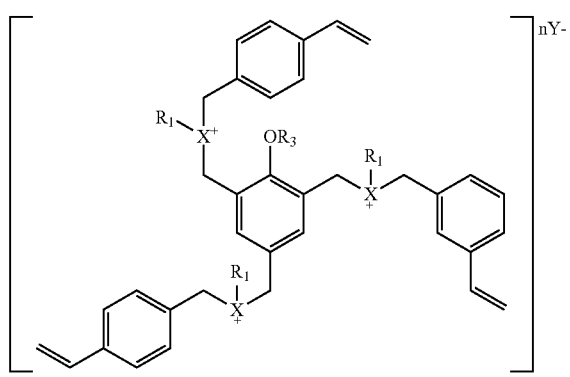

(I)

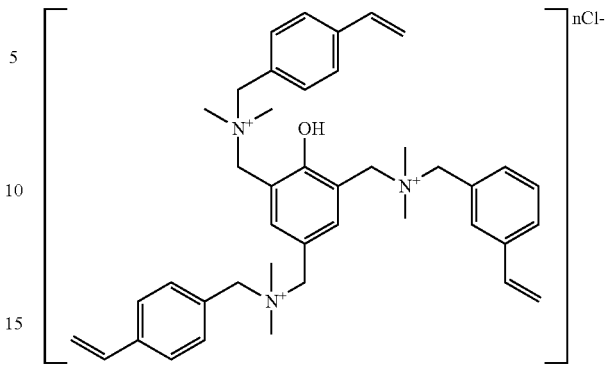

(II)

According to a third aspect, an ionomeric membrane is formed from the polymerisation of a compound as defined above, and optionally other monomers.

According to a fourth aspect, a method of producing a compound as defined in above comprises reacting a compound having a reactive alkyl halide group with a molecule containing two or more ionic groups selected from a tertiary trialkyl amine group, a tertiary trialkyl phosphine group or a secondary dialkyl sulphide group.

DESCRIPTION OF THE PREFERRED EMBODIMENTS

As used herein, an alkyl group can be straight-chain or branched, and contains from 1 to 6 carbon atoms, preferably 1 to 4 carbon atoms. It includes groups such as methyl, ethyl, isopropyl and t-butyl.

The compounds of the invention are useful as cross-linkers. Preferably, they are used to cross-link hydrophilic membranes. Preferably the are used to cross-link anionic membranes. These membranes may be used in an electrolyser or a fuel cell. Preferably, they are used in an electrolyser.

Preferably, the compound comprises 2 or 3 covalently bonded polymerisable vinyl groups.

Preferably, the compound comprises 1, 2 or 3 covalently bonded ionic groups.

In a preferred embodiment, the covalently bonded ionic group is a quaternary ammonium group.

The compounds of formula I and II are useful as a cross-linker.

In a preferred embodiment, a cross-linker of the invention is used to cross-link an anionic membrane.

In a preferred embodiment, an ionomeric membrane is formed from the polymerisation of a compound as defined above, one or more monomers comprising a cationic group, preferably selected from a quaternary ammonium group; a quaternary phosphonium group; or a tertiary sulphonium group and/or one or more non-ionic monomers.

Preferably, the one or more monomers comprising a cationic group includes vinylbenzyltrimethylammonium chloride (BV) and/or the one or more non-ionic monomers includes styrene.

Preferably, an ionomeric membrane of the invention is formed from components comprising a polymerisation initiator, preferably a UV initiator such as UV8.

Any suitable polymerisation process can be used to form an ionomer of the invention. Preferably, polymerisation is by thermal or UV.

The ionomeric membranes of the invention are preferably polymerised from their monomers/cross-linking monomers using UV irradiation.

A method of producing a cross-linker of the invention comprises reacting a compound having a reactive alkyl halide group with a molecule containing two or more ionic groups selected from a tertiary trialkyl amine group, a tertiary trialkyl phosphine group or a secondary dialkyl sulphide group.

In a preferred embodiment, the molecule containing two or more ionic groups is Tris(dimethylaminomethyl)phenol (TDMAP), 1,4-Diazabicyclo[2.2.2]octane (DABCO), tetramethylthiourea, tetramethylurea or 1,3,5-Trimethylhexahydro-1,3,5-triazine (TMHHT).

The reaction may be carried out in any solvent. Preferably, the reaction is carried out in a polar solvent. More preferably, the solvent is an alcohol, most preferably methanol.

In one embodiment, the reaction is:

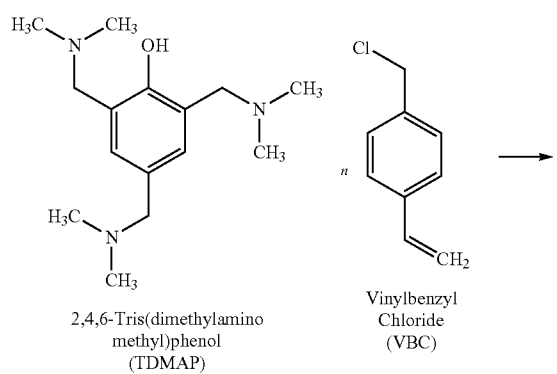

2,4,6-Tris(dimethylamino methyl)phenol (TDMAP)

Vinylbenzyl Chloride (VBC)

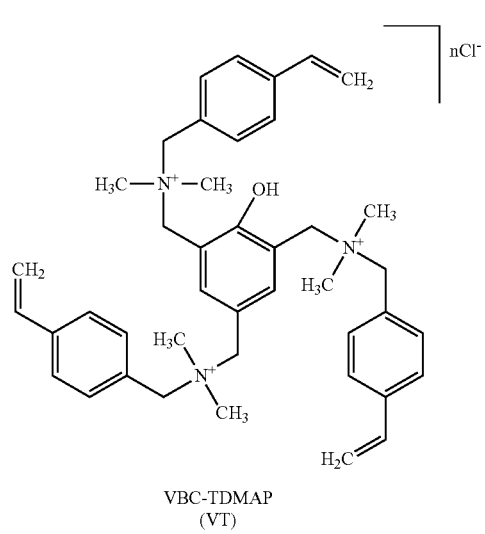

VBC-TDMAP (VT)

The TDMAP may be substituted by 1,4-Diazabicyclo[2.2.2]octane (DABCO), tetramethylthiourea, tetramethylurea or 1,3,5-Trimethylhexahydro-1,3,5-triazine (TMHHT). The skilled person will know suitable reaction conditions for carrying out these reactions, and the reaction shown above.

The structures of the tertiary amines mentioned above are:

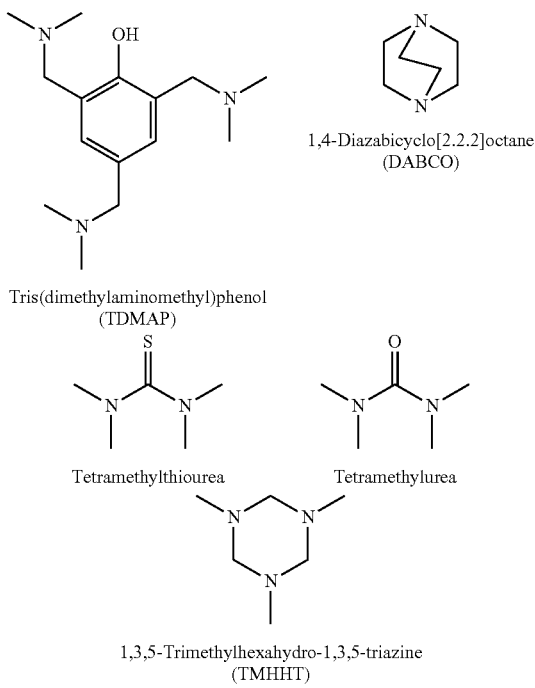

Tris(dimethylaminomethyl)phenol (TDMAP)

1,4-Diazabicyclo[2.2.2]octane (DABCO)

Tetramethylthiourea

Tetramethylurea 1,3,5-Trimethylhexahydro-1,3,5-triazine (TMHHT)

Without wishing to be bound by theory, the reactions above are preferably carried out in polar solvents (e.g. alcohols) as the use of non-polar solvents results in the precipitation of the resultant ionic species. The use of methanol allows the production of the cross-linker as a highly concentrated solution (ca. 70%). The solid ionic cross-linker is not isolated but used directly as the produced methanolic solution.

The membranes produced using the cross-linkers of the invention have superior mechanical properties, greater ionic capacity and greater control of hydration properties.

The invention will now be illustrated by the following example.

EXAMPLE

Experimental for forming an anionic membrane according to the invention:

2,4,6-Tris(dimethylaminomethyl)phenol (TDMAP) (8.46 g, 31.9 mmol) and methanol (10.87 g) were placed in a round bottom flask fitted with a magnetic stirrer, thermometer and pressure equalising dropping funnel. The solution was cooled to below 10° C. in an ice bath. Purified vinylbenzyl chloride (VBC) (95.9 mmol) was added dropwise maintaining the temperature below 15° C. When the addition was complete the reaction mixture was allowed to warm to room temperature in the ice bath and stirred overnight. To the ionic cross-linker (VBC-TDMAP) solution was added methanol (10.87 g), styrene (24.17 g, 23.2 mmol) and vinylbenzyltrimethylammonium chloride (BV) (30.22 g, 142.7 mmol). The mixture was stirred until completely dissolved. UV8 (0.78 g, 3.8 mmol) was added and again stirred until completely dissolved.

The mixture was sealed in a UHMW polyethylene bag and cure under a UV lamp at 100% intensity for 23 minutes.

The membrane formed is called ITM12. Following the same method, but substituting DVB for VBC-TDMAP, formed ITM10.

Figure 2:
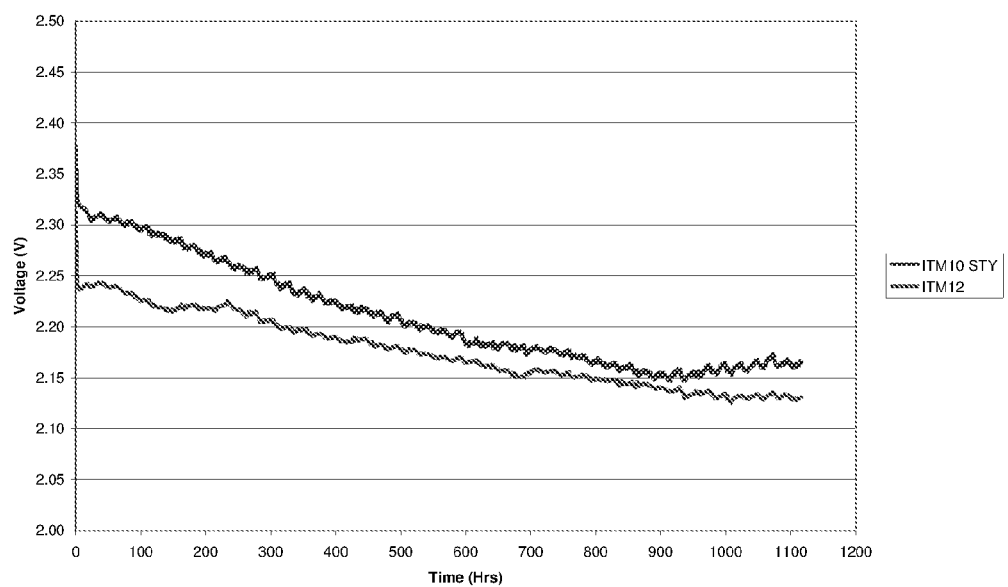

Membrane testing:

FIGS. 1 and 2 show the results of the membrane tests.

In FIG. 1, the top trace is for ITM12, the middle trace is for ITM10 with styrene added, and the bottom trace is for ITM010.

ITM10 membrane is a hydrophilic membrane, which is cross-linked using DVB. This is the comparative example.

ITM12 membrane is a hydrophilic membrane, which is cross-linked using VT, i.e. a compound of the invention. Tensile testing of ITM10 membranes show a stress at break of 4.5 MPa and a strain at break of 7% indicative of the weak brittle membrane it is. The addition of more styrene to ITM10 slightly increases both the stress and the strain at break. The ITM12 membrane has both increased stress and strain over the DVB cross-linked membranes.

Electrolyser efficiency is shown in FIG. 2. Electrolyser efficiency is improved for the ionic cross-linked membrane (ITM12) when compared with the DVB cross-linked membrane (ITM10). ITM10 is the top trace on FIG. 1 and ITM12 is the bottom trace.

The invention claimed is:

1. Use of a compound comprising two or more covalently bonded polymerisable vinyl groups and one or more covalently bonded ionic groups, as an ionic cross-linker in a method of crosslinking a polymer membrane;

wherein the covalently bonded ionic group is a quaternary ammonium group selected from one or more of quaternized tris(dimethylaminomethyl)phenol (TDMAP), 1,4diazabicyclo[2.2.2]octane (DABCO), tetramethylthiourea, tetramethylurea and 1,3,5trimethylhexahydro-1,3,5-triazine (TMHHT).

2. Use according to claim 1, wherein the compound comprises 2 or 3 covalently bonded polymerisable vinyl groups.

3. Use according to claim 1, wherein the compound comprises 1,2 or 3 covalently bonded ionic groups.

4. Use of a compound comprising two or more covalently bonded polymerisable vinyl groups and one or more covalently bonded ionic groups, as an ionic cross-linker linker in a method of crosslinking a polymer membrane, wherein the compound has the formula I:

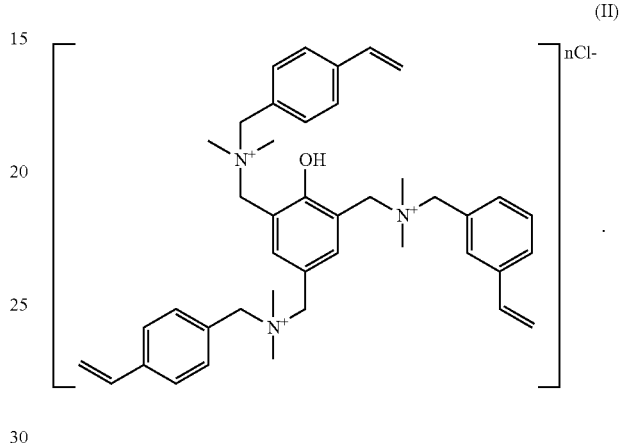

(I)

wherein:

X is $NR_2$, $PR_2$ or S;

each $R_1$ and $R_2$ is independently $C_1$ to $C_6$ alkyl;

$R_3$ is H or $C_1$ to $C_6$ alkyl; and

Y is a counterion.

5. Use of a compound according to claim 1, which has the formula II:

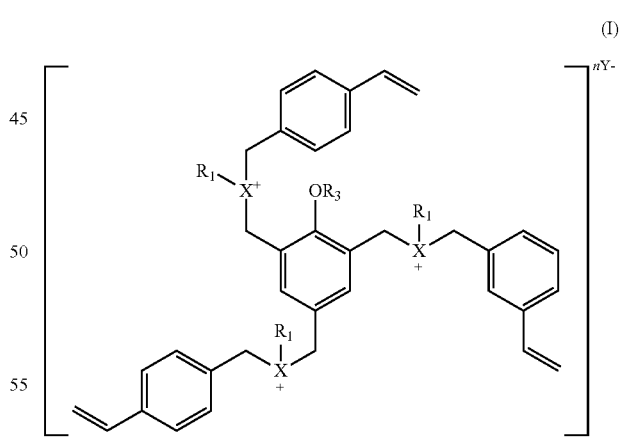

(II)

6. Use according to claim 1, wherein the cross-linker is used to cross-link an anionic membrane.

7. A compound of formula I:

(I)

wherein:

X is $NR_2$, $PR_2$ or S;

each $R_1$ and $R_2$ is independently $C_1$ to $C_6$ alkyl;

$R_3$ is H or $C_1$ to $C_6$ alkyl; and

Y is a counterion;

or of formula II:

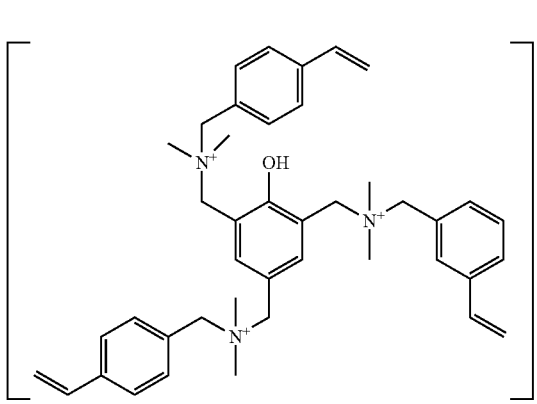

(II)

8. An ionomeric membrane formed from the polymerisation of a compound as defined in claim 1, and optionally other monomers.

9. An ionomeric membrane formed from the polymerisation of a compound as defined in claim 1, one or more monomers comprising a cationic group, selected from the group consisting of a quaternary ammonium group; a quaternary phosphonium group; and a tertiary sulphonium group and/or one or more non-ionic monomers.

10. An ionomeric membrane according to claim 9, wherein the one or more monomers comprising a cationic group includes vinylbenzyltrimethylammonium chloride (BV) and/or the one or more non-ionic monomers includes styrene.

11. A method of producing the compound as defined in claim 1 comprising reacting a compound having a reactive alkyl halide group with a molecule containing two or more ionic groups selected from the group consisting of a tertiary trialkyl amine group, a tertiary trialkyl phosphine group and a secondary dialkyl sulphide group.

12. A method according to claim 11, wherein the molecule containing two or more ionic groups is selected from the group consisting of tris(dimethylaminomethyl)phenol (TDMAP), 1,4diazabicyclo[2.2.2]octane (DABCO), tetramethylthiourea, tetramethylurea and 1,3,5-trimethylhexahydro-1,3,5-triazine (TMHHT).

13. A method according to claim 11, wherein the reaction is carried out in a polar solvent.

14. A method according to claim 13, wherein the solvent is an alcohol.

15. A method according to claim 14, wherein the solvent is methanol.

16. A method according to claim 11, wherein the reaction is:

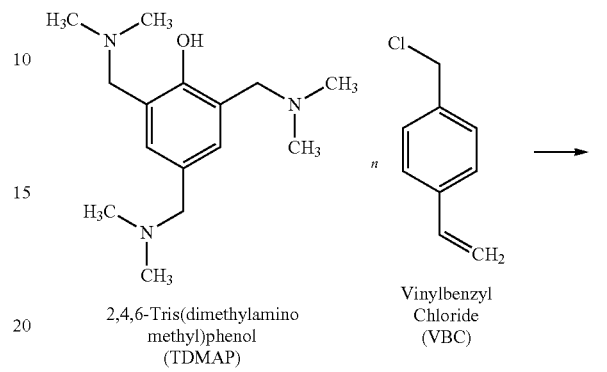

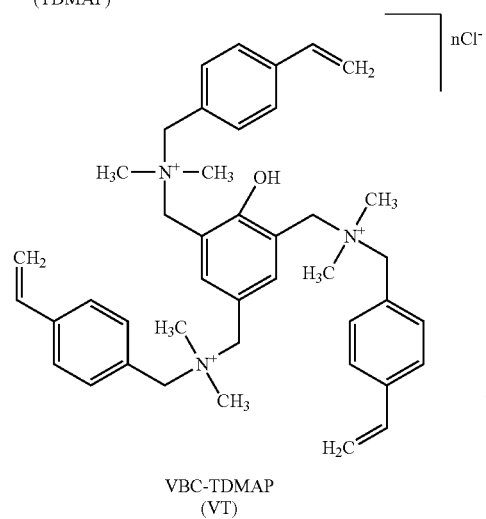

17. A method according to claim 16, wherein the TDMAP is substituted by a compound selected from the group consisting of by 1,4-diazabicyclo[2.2.2]octane (DABCO), tetramethylthiourea, tetramethylurea and 1,3,5-trimethylhexahydro-1,3,5-triazine (TMHHT).

* * * * *